_(12)_ United States Patent
Imai et al.

(10) Patent No.: US 8,349,346 B2
(45) Date of Patent: Jan. 8, 2013

(54) ANTIMICROBIAL COMPOSITION, PROCESS FOR PREPARING THE SAME, AND UTILIZATION THEREOF

(75) Inventors: Hiroshi Imai, Tokyo (JP); Kazushi Kimura, Tokyo (JP)

(73) Assignee: Koken Ltd., Tokyo (JP)

( * ) Notice: Subject to any disclaimer, the term of this patent is extended or adjusted under 35 U.S.C. 154(b) by 345 days.

(21) Appl. No.: 12/613,014

(22) Filed: Nov. 5, 2009

(65) Prior Publication Data

US 2010/0124562 A1    May 20, 2010

(30) Foreign Application Priority Data

Nov. 18, 2008   (JP) ................................. 2008-294075

(51) Int. Cl.
*A01N 37/02* (2006.01)
*A01N 25/34* (2006.01)
*A01P 1/00* (2006.01)
*A61B 19/00* (2006.01)

(52) U.S. Cl. ..................... 424/411; 424/78.37; 128/849; 514/558

(58) Field of Classification Search .................. None
See application file for complete search history.

(56) References Cited

U.S. PATENT DOCUMENTS

| | | | | |
|---|---|---|---|---|
| 5,543,494 A | * | 8/1996 | Perego et al. | 528/354 |
| 5,844,068 A | * | 12/1998 | Otera et al. | 528/361 |
| 5,922,776 A | * | 7/1999 | Wellinghoff et al. | 514/772.3 |
| 2006/0083710 A1 | * | 4/2006 | Joerger et al. | 424/76.1 |
| 2008/0142023 A1 | * | 6/2008 | Schmid et al. | 128/849 |

FOREIGN PATENT DOCUMENTS

| | | |
|---|---|---|
| JP | 05-097619 | 4/1993 |
| JP | 06-014979 | 1/1994 |
| JP | 07-258526 | 10/1995 |
| JP | 08-325848 | 12/1996 |
| JP | 09-095606 | 4/1997 |
| JP | 10-139867 | 5/1998 |
| JP | A 10-139867 | 5/1998 |
| JP | 10-218977 | 8/1998 |
| JP | 10-236904 | 9/1998 |
| JP | 2000-328422 | 11/2000 |
| JP | 2001-261379 | 9/2001 |
| JP | 2004-238316 | 8/2004 |
| JP | 2005-112791 | 4/2005 |
| JP | 2005-514402 | 5/2005 |
| WO | WO 03/055941 | 7/2003 |

OTHER PUBLICATIONS

Notification of Reasons for Rejection issued by the Japanese Patent Office in Japanese App. No. 2009-258728, mailed Jul. 31, 2012.

* cited by examiner

*Primary Examiner* — Ernst Arnold
*Assistant Examiner* — Hong Yu
(74) *Attorney, Agent, or Firm* — Greer, Burns & Crain, Ltd.

(57) ABSTRACT

A highly antimicrobial composition having characteristics of a lactic acid polymer such as biodegradability is prepared by combining a lactic acid oligomer with a metal salt thereof.

6 Claims, No Drawings

ANTIMICROBIAL COMPOSITION, PROCESS FOR PREPARING THE SAME, AND UTILIZATION THEREOF

FIELD OF THE INVENTION

The present invention relates to an antimicrobial composition, a process for preparing the same, and utilization thereof.

BACKGROUND OF THE INVENTION

To meet the recent demand for antimicrobial property in various fields, there have been proposed various antimicrobial agents (including antifungal agents and antimicrobial agents).

Among them, polylactic acids resulting from self-polycondensation of lactic acid hydrolyze easily and possess biodegradability and bioabsorbability, so are used as medical materials, e.g., operating thread. These polylactic acids possess a degree of polymerization high enough for themselves to have formability. Recently, however, studies have been made also about those having a relatively low degree of polymerization, i.e., lactic acid oligomers (see, for example, JP 10-139867A).

In JP 10-139867A, attention is paid not only to the antimicrobial property of lactic acid oligomers but also to sustained release and washing effect thereof. As to antimicrobial property, however, it is actually not always considered satisfactory.

DISCLOSURE OF THE INVENTION

Objects of the Invention

It is an object of the present invention to remarkably improve the antimicrobial property of lactic acid polymers while retaining the characteristics of the polymers, e.g., biodegradability.

SUMMARY OF THE INVENTION

The present invention, in a first aspect thereof, resides in an antimicrobial composition comprising a lactic acid oligomer and a metal salt thereof.

The present invention, in a second aspect thereof, resides in a process for preparing an antimicrobial composition, which process comprises mixing lactic acid and a metal salt thereof with each other and heating the resulting mixture to discharge water to the exterior of the system, thereby allowing dehydrocondensation to take place to form an oligomer.

The present invention, in a third aspect thereof, resides in a process for imparting antimicrobial property to an article, which process comprises mixing, impregnating, or coating, the above antimicrobial composition into or onto the article.

Effects of the Invention

By combining a lactic acid oligomer and a metal salt thereof with each other, not only antimicrobial property is greatly improved, but also, even when the resulting composition is mixed into a formable polymer or a film-forming polymer, it is possible to impart remarkably improved antimicrobial property to those polymers without impairing their formability or quality.

PREFERRED EMBODIMENTS OF THE INVENTION

The antimicrobial composition according to the present invention contains as essential ingredients a lactic acid oligomer and a metal salt thereof.

As the metal which constitutes the metal salt of the lactic acid oligomer there may be used, for example, any of silver, copper, zinc, gold, platinum, tin, nickel, and iron, which have heretofore been known to exhibit an antimicrobial action in an ionic state. But copper, zinc, and iron, are preferred, with copper being particularly preferred.

The antimicrobial composition according to the present invention can be prepared by mixing free lactic acid and a lactic acid metal salt with each other and heating the resulting mixture, thereby allowing a dehydrocondensation reaction to take place. The heating temperature is not specially limited if only in can induce the dehydrocondensation reaction. It is usually in the range of 100° C. to 200° C. For discharging produced water to the exterior of the system and thereby accelerating the condensation reaction, it is preferable to maintain the system in a pressure-reduced state.

As the lactic acid there may be used any of D, L, and DL, forms.

The degree of polymerization of the resulting oligomer can be controlled by adjusting the proportion of the lactic acid metal salt relative to lactic acid. In the present invention, it is preferable to use 0.1 to 1.0 parts by weight, more preferably 0.2 to 0.5 parts by weight, of the lactic acid metal salt relative to the weight of free lactic acid.

The metal salt of the lactic acid oligomer usually has one metal atom for each oligomer molecule.

An average polymerization degree of the oligomer is about 2 to 100, preferably about 5 to 50. The composition prepared by the above process is usually a mixture of a lactic acid oligomer and a metal salt thereof both almost equal in the degree of polymerization and the polymerization degree distribution.

The antimicrobial composition according to the present invention can also be prepared by beforehand preparing a lactic acid oligomer through a self-polycondensation reaction using free lactic acid to afford a lactic acid oligomer and then introducing copper ions into (a part of) carboxyl ends thereof.

In the present invention it is preferable to use 0.1 to 1.0 parts by weight, more preferably 0.2 to 0.5 parts by weight, of the lactic acid metal salt relative to 1 part by weight of free lactic acid. Although the metal salt content is rather small, the presence thereof brings about a great improvement of antimicrobial property.

The antimicrobial composition according to the present invention, i.e., a mixture of a lactic acid oligomer and a metal salt thereof, is a low melting (usually 100° C. or lower) solid product and can be easily mixed with a formable polymer or a film-forming polymer, e.g., thermosetting elastomer, thermoplastic elastomer, or thermoplastic resin. Even if the mixture is mixed into such a formable or film-forming polymer, they will scarcely impair the formability and film-formability of those polymers or the quality of the resulting article. Particularly, incorporating the mixture into silicone rubber which is a thermosetting elastomer to afford a formed article or a film is one of preferred embodiments of use.

The antimicrobial composition according to the present invention can also be impregnated into fiber articles such as knitted gauze, nonwoven fabric or woven fabric, in the form of a solution or dispersion thereof, followed by squeezing and drying to afford antimicrobial fiber articles.

The amount of the antimicrobial composition to be incorporated into the aforesaid formable, film-forming polymer or fiber article is preferably about 0.5 to 3 wt %. The final product thus produced has usually an antimicrobial activity value (JIS Z 2801) of at least 2 and is effective to both of gram-positive and gram-negative bacterias.

The antimicrobial composition according to the present invention is applicable to various uses in which antimicrobial agents have heretofore been used. As examples of preferred uses are mentioned clothes, textile and nonwoven fabric products such as disposable masks, knitted gauzes, particulate respirators, gas masks, particulate filters, various paper filters and various formed products.

The present invention will be described below by way of Examples.

Tests for autimicrobial activity used in Examples are as follows:

(1) Testing method 1: Absorption method (JIS L 1902) (quantitative test)

Kind of bacteria: *Escherichia coli*

Test piece: about 18 mm square, 3 test specimens for each sample standard cloth 6 test specimens Viable bacteria count measuring method: Plate count method Test Operation:

0.2 ml of test bacteria liquid was soaked into three sterilized standard cloth test specimens, followed by stirring together with 20 ml of wash-out liquid, and the number of viable bacteria was measured by Plate count method.

On the other hand, 0.2 ml of test bacteria liquid was soaked into three sterilized standard cloth test specimens and three test specimens for each sample, followed by culture (conditions: 37±1° C., 18±1 hrs) together with 20 ml of washing liquid, and the number of viable bacteria was measured by Plate count method.

Evaluation Method:

(i) Criterion of Test Existence

Growth value $[F] > 1.5$ $$F = Mb - Ma$$

Ma: average value of common logarithms of number of living bacteria of three specimens immediately after inoculation of inoculum on standard cloth Mb: average value of common logarithms of number of living bacteria of three specimens after 18-hour incubation on standard cloth (ii) Activity Value:

Bacteriostatic activity value $S = Mb - Mc$

Bactericidal activity value $L = Ma - Mc$

Mc: average value of common logarithms of number of living bacteria of three specimens after 18-hour incubation on antibacterial deodorant finished sample or on microbial control finished sample (2) Testing method 2: Film attaching method (JIS Z 2801)

Example 1

500 g of DL-lactic acid and 1 g of copper lactate were placed into a four-necked 1000 ml flask. A stirring rod equipped with a thermometer, a pressure reducing port, a nitrogen gas inlet port and a pressure-reducing seal was attached to the flask and heating was conducted at 145° C. for 3 hours to remove water contained in the DL-lactic acid. Then, a dehydrocondensation reaction was performed by heating and reducing pressure under the conditions of 145° C., 150 mmHg, 3 hours, 150° C., 15 mmHg, 3 hours, and finally 185° C., 15 mmHg, 1.5 hours, to afford a mixture of a lactic acid oligomer and a copper salt thereof. The molecular weights were measured and found to be distributed approximately in the range of 500 to 3000. Both lactic acid oligomer and copper salt thereof were found to have an average polymerization degree of about 20.

Comparative Example 1

A lactic acid oligomer was prepared in the same way as in Example 1 except that the copper lactate was not used.

Bacteriostatic Test:

Official gauze (290×290 mm) was immersed in each of a solution (solvent: acetonitrile) of the mixture of the lactic acid oligomer and the copper salt thereof prepared in Example 1 and a solution (solvent: acetonitrile) of the lactic acid oligomer prepared in Comparative Example 1 and was then dried to remove the solvent, affording samples with an adhered oligomer's amount of 0.5 wt %.

Subsequently, a test of antimicrobial activity was conducted for both samples in Example 1 and Comparative Example 1.

The results are shown in Table 1.

TABLE 1

| Sample | Bacteria Count[cells/ml] |
|---|---|
| standard cloth, viable bacteria count just after inoculation [A] | $1.2 \times 10^5$ |
| standard cloth, viable bacteria count after culture [B] | $2.3 \times 10^8$ |
| Viable bacteria count in the comparative oligomer [C] | $2.1 \times 10^4$ |
| Viable bacteria count in the oligomer mixture of Example 1 [C] | <20 |

(The number of viable bacteria in case of bacteria count being <1 is indicated as <20 and an antimicrobial activity value is calculated, assuming that the bacteria count is 20.)

Next, a bacteriostatic value and a bactericidal activity value were calculated in accordance with the JIS evaluation method and using the following equations:

Bacteriostatic activity value: $S = \log B - \log C$

Bactericidal activity value: $L = \log A - \log C$

The results are shown in Table 2.

TABLE 2

| Sample | Bacteriostatic Activity Value S | Bactericidal Activity Value L |
|---|---|---|
| Oligomer of Comparative Example 1 | 4.0 | 0.76 |
| Oligomer mixture of Example 1 | 7.1 | 3.8 |

Example 2

The mixture of the lactic acid oligomer and the copper salt thereof prepared in Example 1 was added to liquid silicone rubber in amounts of 0.1 wt %, 0.5 wt %, 1 wt %, 2 wt %, and 3 wt %, followed by forming and heat-curing, to afford 170× 200 mm sheets having a thickness of 0.1 mm. Both formability and sheet quality were substantially the same as in the case of liquid silicone rubber alone.

In accordance with JIS Z 2801 the sheets were subjected to an antimicrobial property test using *Escherichia coli*. The results are shown in Table 3.

TABLE 3

*Escherichia coli*

| Sample | | Viable Bacteria Count (Mean Value) [cells] | Value of Antimicrobial Activity |
|---|---|---|---|
| The untreated testpiece | just after | $1.6 \times 10^7$ | — |
| | after culture | $2.8 \times 10^7$ | — |
| | 3% | <10 | 6.3 |
| | 2% | <10 | 6.3 |
| | 1% | <10 | 6.3 |
| | 0.5% | <10 | 6.3 |
| | 0.1% | $1.4 \times 10^6$ | 1.1 |

(The number of viable bacteria in case of the number of colony being <1 is indicated as <10 and an antimicrobial activity value is calculated, assuming that the viable bacteria count is 10.)

By using the same samples and *Staphylococcus aureus* (NBRC 12732, gram-positive bacterias), antimicrobial property tests were conducted in accordance with JIS Z 2801.

The results are shown in Table 4.

TABLE 4

| | Sample | | Visible Bacteria Count [cells/ml] | Bactericidal Activity Value |
|---|---|---|---|---|
| 1 | The untreated test piece | just after | $2.3 \times 10^5$ | — |
| | | after culture | $1.8 \times 10^6$ | — |
| 2 | Oligomer | 3% | <10 | 5.2 |
| | | 2% | <10 | 5.2 |
| | | 1% | <10 | 5.2 |
| | | 0.5% | <10 | 5.2 |
| | | 0.25% | $3.9 \times 10^5$ | 0.67 |

From the above results obtained in the Examples and Comparative Example it is seen that the antimicrobial property is greatly improved by mixing a lactic acid oligomer metal salt into the lactic acid oligomer as compared with using the lactic acid oligomer alone and that even in case of mixing the composition according to the present invention into, for example, silicon rubber, there is obtained excellent antimicrobial property without impairing the formability and quality.

Example 3

Glass fibers extremely small in diameter were integrally formed into a round pleat shape by the paper making technique, affording a cylindrical formed particulate filter (designated "α ring filter").

A lactic acid-copper lactate oligomer was prepared in the same way as in Example 1 and a solution thereof in ethanol having an adjusted concentration was prepared.

The α ring filter was immersed in the ethanol solution and then dried, whereby the lactic acid-copper lactate oligomer was adhered to the α ring filter.

The oligomer was used in amounts of 0.5%, 1.5%, and 3.2% (amounts based on the weight of the α ring filter).

Then, a test of antimicrobial property was conducted in accordance with JIS L 1902.

The results are shown in Table 5. Growth value: F=1.5

TABLE 5

| | Sample | | Viable Bacteria Count [cells/ml] | Ma, Mb, Mc | Bactericidal Activity Value |
|---|---|---|---|---|---|
| 1 | standard cloth | just after | $5.2 \times 10^5$ | 5.7 | — |
| | | after culture | $1.3 \times 10^7$ | 7.2 | — |
| 2 | Oligomer 0.5% | | $1.2 \times 10^6$ | 6.1 | −0.4 |
| 3 | Oligomer 1.5% | | <20 | 1.3 | 4.4 |
| 4 | Oligomer 3.2% | | <20 | 1.3 | 4.4 |

(The number of viable bacteria in case of the number of colony being <1 is indicated as <20 and an antimicrobial activity value is calculated, assuming that the number of viable bacteria is 20.)

Example 4

There was provided a disposable filtering face piece respirator with a bowl-like nonwoven fabric filter attached to a plate-like face-contacting felt piece for contact with the face of a wearer.

A lactic acid-copper lactate oligomer was prepared in the same way as in Example 1 and, using this oligomer, a solution thereof in ethanol was prepared (2 mg/ml).

This ethanol solution was applied to the above mask several times with a spray. In this way the oligomer was applied to the mask in amounts of 0.04%, 0.06%, and 0.13% (based on the mask weight).

Then, a test of antimicrobial property was conducted in accordance with JIS L 1902.

The results of the bacteria count measurement are shown in Table 6.

TABLE 6

| Sample | | Bacteria Count [cells/ml] |
|---|---|---|
| standard cloth | just after [A] | $6.2 \times 10^3$ |
| | after culture [B] | $2.8 \times 10^7$ |
| 0.04%, viable bacteria count after culture [C] | | $2.0 \times 10^4$ |
| 0.06%, viable bacteria count after culture [C] | | $1.1 \times 10^5$ |
| 0.13%, viable bacteria count after culture [C] | | <20 |

Bacteriostaic activity value S = log[B] − log[C]
Bactericidal activity value L = log{A} − log[C]

TABLE 7

| Sample | Bacteriostatic Activity Value S | Bactericidal Activity Value L |
|---|---|---|
| 0.4% | 3.2 | −0.51 |
| 0.06% | 2.1 | −1.6 |
| 0.13% | 6.2 | 2.5 |

The invention claimed is:

1. An antimicrobial composition comprising a lactic acid oligomer and a copper salt thereof.

2. An antimicrobial composition as set forth in claim 1, wherein an average polymerization degree of the lactic acid oligomer and that of the copper salt thereof are each in the range of 2 to 100.

3. An antimicrobial composition as set forth in claim 1, wherein, based on 1 part by weight of the lactic acid oligomer, 0.1 to 1.0 part by weight of the copper salt thereof is present.

4. A process for preparing an antimicrobial composition in claim 1, which comprises mixing lactic acid and a copper salt thereof with each other and heating the resulting mixture to remove water to the exterior of the system, thereby allowing dehydrocondensation to take place to form an oligomer.

5. A process for imparting antimicrobial property to an article, which process comprises mixing, impregnating, or coating, the antimicrobial composition recited in claim 1 into or onto the article.

6. A process as set forth in claim 5, wherein the article is a fibrous filter.

* * * * *